United States Patent [19]

Ridgway et al.

[11] 4,422,945

[45] Dec. 27, 1983

[54] STABILIZATION OF PLEUROMUTILIN DERIVATIVES AGAINST OXIDATION BY SODIUM HYPOCHLORITE IN AQUEOUS SOLUTION

[75] Inventors: Frank Ridgway, Birkenhead; Richard D. G. Woolfenden, Bridgend, both of England

[73] Assignee: E. R. Squibb & Sons, Inc., Princeton, N.J.

[21] Appl. No.: 424,122

[22] Filed: Sep. 27, 1982

Related U.S. Application Data

[62] Division of Ser. No. 241,167, Mar. 6, 1981, Pat. No. 4,390,558.

[30] Foreign Application Priority Data

Mar. 14, 1980 [GB] United Kingdom ............... 8008792

[51] Int. Cl.$^3$ ............................................... C02F 1/50
[52] U.S. Cl. .................................................. 210/764
[58] Field of Search ............... 210/749, 764; 424/149, 424/162, 164, 305, 311, 331; 426/60, 532, 541, 544, 422

[56] References Cited

U.S. PATENT DOCUMENTS 2,927,859  3/1960  Gordon .......................... 424/162 X
3,919,290  11/1975 Egger et al. .................... 424/311 X
3,987,194  10/1976 Baughn et al. .................. 424/331 X

*Primary Examiner*—Thomas G. Wyse
*Attorney, Agent, or Firm*—Lawrence S. Levinson; Burton Rodney

[57] ABSTRACT

A composition and method which provides a compound of the formula I:

wherein
either $R_1$ is ethyl or vinyl,
$n$ is an integer from 2 to 5 and
each of $R_2$ and $R_3$ is alkyl of 1 to 10 carbon atoms.

Also provided is a hypochlorite scavenger in solution with the formula I compound which stabilizes the compound against oxidation by sodium hypochlorite.

A preferred solution contains the compound of formula I wherein $R_1$ is vinyl, $R_2$ and $R_3$ are ethyl as a salt of hydrogen fumarate i.e. tiamulin hydrogen fumarate. The solution is added to drinking water which is fed to farm animals as treatment for mycoplasma infection.

7 Claims, No Drawings

STABILIZATION OF PLEUROMUTILIN DERIVATIVES AGAINST OXIDATION BY SODIUM HYPOCHLORITE IN AQUEOUS SOLUTION

This is a division of application Ser. No. 241,167, filed Mar. 6, 1981, U.S. Pat. No. 4,390,558.

BACKGROUND OF THE INVENTION

The sterilization of drinking water pipelines and utensils for farm animals is sometimes carried out using a solution of sodium hypochlorite. There are also occasions in which pond water is similarly sterilized for animal consumption in situations where water supply mains are not available.

Baughn discloses in U.S. Pat. No. 3,987,194 issued Oct. 19, 1976 that octahydro-5,8-dihydroxy-4,6,9,10-tetramethyl-6-vinyl-3a,9-propano-3aH-cyclopentacycloocten-1(4H)-one,8[[2-(diethylamino)ethyl]-thio]acetate; or octahydro-5,8-dihydroxy-4,6,9,10-tetramethyl-6-vinyl-3a,9-propano-3aH-cyclopentacycloocten-1(4H)-one,8-[[2-[4-(2-hydroxyethyl)-1-piperazinyl]-ethyl]thio]acetate is useful against swine dysentery. And that the agents can be added to the drinking water.

U.S. Pat. No. 3,919,290 issued Nov. 11, 1975, discloses various 14-deoxymutilins, which are pleuromutilin derivatives. The compounds are disclosed as being useful because of their pharmacological activity in animals, and more specifically, they are said to be useful as antibiotics with antibacterial action. The reference discloses the compounds to be useful both prophylactically and therapeutically in domestic animals, particularly pigs and poultry.

14-Deoxy-14-[(2-diethylaminoethyl)mercaptoacetoxy]mutilin, and pharmaceutically acceptable salts thereof, is disclosed by the reference. The base compound has the non-proprietary name tiamulin.

OBJECTS OF THE INVENTION

It has been observed that residues of sodium hypochlorite in drinking water can adversely affect the therapeutic activity of tiamulin hydrogen fumarate by imparting upon the antibiotic an oxidative decomposition to the corresponding sulphoxide.

It is an object of the invention to provide a means of removing the adverse effects of sodium hypochlorite by the use of selected scavengers.

These scavengers are chosen such that they can either be added to the drinking water prior to the incorporation of the antibiotic or they can be added with the antibiotic in which case they are able to preferentially react with the sodium hypochlorite.

It is an object of the invention to provide a treatment for mycoplasma infection in farm animals.

DETAILED DESCRIPTION OF THE INVENTION

In accordance with the invention there is provided a compound of the formula I:

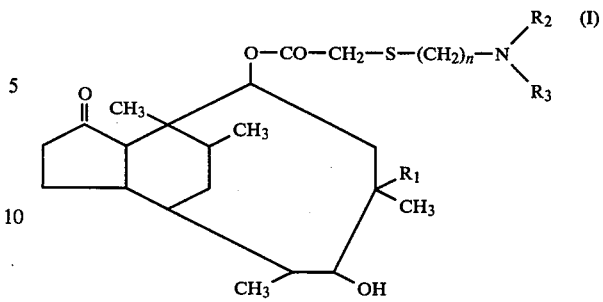

wherein
either $R_1$ is ethyl or vinyl,
n is an integer from 2 to 5 and
each of $R_2$ and $R_3$ is alkyl of 1 to 10 carbon atoms.

Also provided is a hypochlorite scavenger in solution with the formula I compound.

A preferred solution contains the compound of formula I wherein $R_1$ is vinyl, $R_2$ and $R_3$ are ethyl as a salt of hydrogen fumarate i.e. tiamulin hydrogen fumarate.

There is interaction between the compound of formula I, for example Octahydro-5,8-dihydroxy-4,6,9,10-tetramethyl-6-vinyl-3a,9-propano-3a$\underline{H}$-cyclopentacycloocten-1(4$\underline{H}$)-one, 8-[[[2-(diethylamino)ethyl]-thio]acetate], fumarate (1:1) hereinafter called tiamulin hydrogen fumarate, and sodium hypochlorite which is quantitative and spontaneous at room temperature. The degradation products resulting from the interaction are the sulphoxide and the hydrolysis products of the compound of formula I. The former is present in considerable quantities, whereas the latter is only a minor component.

The compounds of formula I can be added in concentrations ranging between 0.0045% by weight and 0.0125% by weight to the drinking water of farm animals for the treatment of mycoplasma infections. It is rendered unstable if residues of the sodium hypochlorite sterilant are present in quantities exceeding 1 ppm. of available chlorine. The reaction is instantaneous and primarily oxidative in nature, the resulting decomposition product being the corresponding sulphoxide. A minor amount of hydrolysis product is also produced.

The extent of the decomposition is dependent on the available chlorine content of the water. This is illustrated by the data given in Tables 1A and 1B which show the effect of various concentrations of available chlorine on the decompositions of (a) 0.01% tiamulin base in 50% aqueous methanol (to solubilize the base) and (b) 0.0125% tiamulin hydrogen fumarate (with 0.0153% lactose B.P.) in water. Thus, the reaction is shown to be quantitative in the presence of sufficient quantities of available chlorine.

TABLE 1A

| % Recovery of tiamulin base (HPLC ASSAY) | PPM available chlorine concentration |
|---|---|
| 93 | 2.5 |
| 85 | 5 |
| 80 | 7.2 |
| 76 | 10 |
| 70 | 12 |
| 57 | 18 |
| 34 | 24 |
| 23 | 30 |

TABLE 1B

| % recovery of tiamulin hydrogen fumarate | PPM available chlorine |
|---|---|
| 92 (HPLC) | 1 |
| 85 (Micro) | 1 |
| 88 (HPLC) | 2 |
| 90 (Micro) | 2 |
| 74 (HPLC) | 3 |
| 76 (Micro) | 3 |
| 66 (HPLC) | 10 |
| 68 (Micro) | 10 |
| 6 (HPLC) | 25 |
| 12 (Micro) | 25 |

Sodium hypochlorite is a well known oxidizing agent which is prepared by the interaction of chlorine gas with aqueous sodium hydroxide solution. The scavenging of sodium hypochlorite to prevent its reaction with the formula I compound can be achieved by the use of suitable reducing agents such as sodium thiosulphate, sodium sulphite, sodium nitrite, acetone sodium bisulphite, ascorbic acid, dithiothreitol, dithioerythritol and urea. Of these materials sodium thiosulphate, acetone sodium bisulphite, ascorbic acid, dithiothreitol and dithioerythritol are able to preferentially react with sodium hypochlorite when added with the the formula I compound. The remaining materials are only suitable when added prior to the addition of the formula I compound.

The suitability of the latter named scavengers depends on their concentration relative to that of the residual sodium hypochlorite. Thus, their scavenging performances can be gauged by the information summarised in Tables 1 to 3 which represent the effect of various concentrations of sodium thiosulphate, acetone sodium bisulphite, and ascorbic acid when added with 0.0125% tiamulin hydrogen fumarate to drinking water containing excessive residues of sodium hypochlorite (i.e. 5 ppm. available chlorine). The data clearly shows that the antibiotic activity is maintained at scavenger concentrations in excess of 40 ppm.

In practice the scavenging of residual sodium hypochlorite must be achieved in sterilized pond water for drinking or in pipelines and utensils through which fresh, unsterilized drinking water may be supplied. These requirements may be achieved in several ways, as for example:

(1) The scavenger and the pleuromutilin compound formulation are dissolved together in a small quantity of sterilized or unsterilized water and the resulting concentrate is then added to the bulk of the sterilized drinking water giving a supply which contains effective antibiotic activity.

(2) The scavenger is dissolved directly in the bulk of the sterilized drinking water either prior to or with the requisite quantity of the pleuromutilin compound formulation, producing a supply which contains effective antibiotic activity.

(3) The scavenger and pleuromutilin compound formulation are dissolved together in a small quantity of fresh water and the resulting concentrate is added to the bulk of the fresh, unsterilized drinking water which when fed through the sterilized pipelines and utensils gives a supply containing the theoretical amount of effective antibiotic activity.

The following examples illustrate the invention.

EXAMPLE 1

Provide 20 liters of pond drinking water containing
(a) 0.0125% Tiamulin hydrogen fumarate
(b) 0.0153% Lactose
(c) 0.004% Sodium thiosulphate
(c) and (a) are prepared as follows:
  0.8 g. of sodium thiosulphate was dissolved in 250 ml. of sterilized pond water.
  5.56 g. of tiamulin hydrogen fumarate was added and stirred until dissolved. The resulting concentrate was added to the bulk of the sterilized pond water to give a 20 liter drinking water supply containing effective antibiotic activity.

EXAMPLE 2

The same method as Example 1 but containing 0.004% of any of the following scavengers: acetone sodium bisulphite, ascorbic acid, dithiothreitol or dithioerythritol.

EXAMPLE 3

The method of Example 1 but in which the sodium thiosulphate and tiamulin hydrogen fumarate are added simultaneously.

EXAMPLE 4

The same as for Example 3 but in which the scavenger is acetone sodium bisulphite, ascorbic acid, dithiothreitol or dithioerythritol.

EXAMPLE 5

The same as for Examples 1–4 but in which the drinking water is fresh mains i.e. city water, for supply to a sterilized delivery system.

EXAMPLE 6

The same as for Examples 1–5 but in which the scavengers are at a concentration of 0.0125%.

EXAMPLE 7

The same as for Examples 1–6 but in which the tiamulin hydrogen fumarate is at a concentration of 0.0045% and the lactose is at a concentration of 0.0255%.

EXAMPLE 8

Provide 20 liters of pond drinking water containing
(a) 0.0125% Tiamulin hydrogen fumarate
(b) 0.0153% Lactose
(c) 0.004% Sodium thiosulphate
(c) and (a) are prepared as follows:
  0.8 g. of sodium thiosulphate was dissolved, with stirring, in 20 liters of sterilized pond water.
  5.56 g. of tiamulin hydrogen fumarate was then added, with stirring, to give a supply containing effective antibiotic activity.

EXAMPLE 9

The same as for Example 8, but in which the scavenger is acetone sodium bisulphite, ascorbic acid, dithiothreitol, dithioerythritol, sodium bisulphite, sodium nitrite or urea, or a combination of any of these.

TABLE 1

Scavenging Effect of Sodium Thiosulphate

| Sample | % Tiamulin Hydrogen Fumarate Recovered | |
|---|---|---|
| | HPLC | Micro |
| Control | 100 | 100 |
| Control + 5 ppm. av. Cl. | 77.3 | 76 |
| Control + 5 ppm. av. Cl. + 3 ppm. Thio | 89.8 | 96 |
| Control + 5 ppm. av. Cl. + 8 ppm. Thio | 92.0 | 89 |
| Control + 5 ppm. av. Cl. + 13 ppm. Thio | 95.0 | 97 |
| Control + 5 ppm. av. Cl. + 26 ppm. Thio | 97.2 | 98 |
| Control + 5 ppm. av. Cl. + 53 ppm. Thio | 100.1 | 99 |

TABLE 2

Scavenging Effect of Acetone Sodium Bisulphite (ASB)

| Sample | % Tiamulin Hydrogen Furmarate Recovered | |
|---|---|---|
| | HPLC | Micro |
| Control | 100.0 | 100 |
| Control + 5 ppm. av. Cl. | 77.0 | 83 |
| Control + 5 ppm. av. Cl. + 4 ppm. ASB | 78.8 | 88 |
| Control + 5 ppm. av. Cl. + 13 ppm. ASB | 89.9 | 99 |
| Control + 5 ppm. av. Cl. + 21 ppm. ASB | 94.6 | 107 |
| Control + 5 ppm. av. Cl. + 42 ppm. ASB | 99.3 | 106 |
| Control + 5 ppm. av. Cl. + 84 ppm. ASB | 105.0 | 107 |

TABLE 3

Scavenging Effect of Ascorbic Acid (AA)

| Sample | % Tiamulin Hydrogen Fumarate Recovered | |
|---|---|---|
| | HPLC | Micro |
| Control | 100.0 | 100 |
| Control + 5 ppm. av. Cl. | 81.2 | 89 |
| Control + 5 ppm. av. Cl. + 3 ppm. AA | — | — |
| Control + 5 ppm. av. Cl. + 8 ppm. AA | 88.0 | 94 |
| Control + 5 ppm. av. Cl. + 13 ppm. AA | — | — |
| Control + 5 ppm. av. Cl. + 26 ppm. AA | 91.2 | 88 |
| Control + 5 ppm. av. Cl. + 53 ppm. AA | 95.6 | 98 |

Examples 1 through 9 show hypochlorite scavenging antibiotic solutions of the present invention. The antibiotic effectiveness is increased by the action of the hypochlorite scavenger. By scavenging hypochlorite a substantial portion of the antibiotic formula I compound is maintained in its unoxidized and unhydrolized state.

Table IA shows that as the concentration of available chlorine increases (in the absence of hypochlorite scavenger) the percentage recovery of tiamulin base decreases. The available chlorine is from hypochlorite.

Table IB shows that as the concentration of available chlorine increases (in the absence of hypochlorite scavenger) the percentage recovery of tiamulin hydrogen fumarate decreases. The percent recovery of tiamulin hydrogen fumarate is measured by both high performance liquid chromatography (HPLC) and microanalysis (micro). In Table I the results are shown for using sodium thiosulphate to scavenge for available chlorine. In Table II the results are shown for using acetone sodium bisulfite to scavenge for available chlorine in the amount of five parts per million. In Table III the results are shown for using ascorbic acid to scavenge for five parts per million of available chlorine.

Table IB shows that as the concentration of available chlorine increases the percent recovery of tiamulin hydrogen fumarate decreases in the absence of hypochlorite scavenger.

Comparing Tables I through III with Table IB, it is seen that when 3 parts per million of available chlorine is present in the absence of a scavenger, only 74 to 76% of the tiamulin hydrogen fumarate is obtained. Whereas Table I shows that in the presence of an even higher concentration of available chlorine (5 parts per million of available chlorine) 99 to 100% of the tiamulin hydrogen fumarate may be covered when sodium thiosulphate scavenger is present. Similarly, Table II shows that all of the tiamulin hydrogen fumarate may be recovered when acetone sodium bisulphite is present. In Table III 95 to 98% of the tiamulin hydrogen fumarate is shown to be recovered from a solution containing five parts per million of available chlorine when ascorbic acid is present in the amount of 53 parts per million. The percent recovery of tiamulin represents the percent of effective tiamulin in the solution. Thus, it also represents the percent of effective antibiotic present in the solution.

In summary, when available chlorine is present the concentration of unoxidized tiamulin hydrogen fuamrate are reduced. The higher the concentration of available chlorine the lower the percentage recovery of tiamulin hydrogen fumarate. The present invention uses a scavenger for available chlorine in solution with compounds of formula I. The scavenger increases the effectiveness of the compound of formula I by increasing the concentration of the compound of formula I which is neither oxidized nor hydrolized. The preferred weight ratio of formula I compound to hypochlorite scavenger is from about 0.1:1 to about 500:1.

We claim:

1. A method of water treatment comprising providing an aqueous solution by providing water and adding to said water a hypochlorite scavenger and 0.0045 to 0.0125% (based on the weight of the aqueous solution) of a compound of the formula

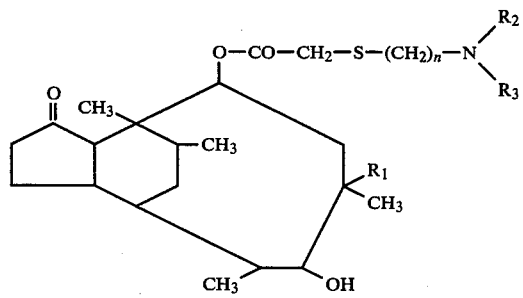

wherein either $R_1$ is ethyl or vinyl, n is an integer from 2 to 5 and each of $R_2$ and $R_3$ is an alkyl of 1 to 10 carbon atoms, and pharmaceutically acceptable salts of said compound, said hypochlorite scavenger being selected from the group consisting of sodium thiosulphate, acetone sodium bisulphite, ascorbic acid, dithiothreitol dithioerythritol, sodium sulphite, sodium nitrate, and urea, said compound being present in a weight ratio to the hypochlorite scavenger of from about 0.1:1 to about 500:1.

2. The method of claim 1 wherein said compound is tiamulin hydrogen fumarate.

3. The method of claim 1 wherein said hypochlorite scavenger is added in a first step and said tiamulin hydrogen fumarate is added in a second step.

4. The method of claim 3 further comprising adding lactose and wherein said lactose is 0.1 to 0.02% by weight of said aqueous solution.

5. The method of claim 1 wherein said scavenger concentration is above 40 ppm of said aqueous solution.

6. The method of claim 1 further comprising providing said aqueous solution to domestic animals as drinking water whereby mycoplasma infections are controlled prophylactically and therapeutically.

7. The method of claim 1 wherein said hypochlorite scavenger is added concurrently with said compound.

* * * * *